United States Patent [19]

Zoeller

[11] Patent Number: 4,902,820
[45] Date of Patent: Feb. 20, 1990

[54] PREPARATION OF α-ACYLOXYCARBONYL COMPOUNDS

[75] Inventor: Joseph R. Zoeller, Kingsport, Tenn.

[73] Assignee: Eastman Kodak Company, Rochester, N.Y.

[21] Appl. No.: 312,982

[22] Filed: Feb. 21, 1989

[51] Int. Cl.$^4$ .................. C07C 69/66; C07C 69/32
[52] U.S. Cl. ............................. 560/185; 560/231; 560/254; 560/255; 560/176
[58] Field of Search ............ 560/185, 231, 254, 255, 560/176

[56] References Cited

PUBLICATIONS

Fuson et al., "The Reduction of Mixed Hindered Benzils", J. Am. Chem. Soc., 71, 1585 (1949).
Reusch et al, "Rearrangements of 4,5-Oxidocholestane-3-one", J. Am. Chem. Soc., 85, 1669 (1963).
Reusch et al., "A Versatile Ketone Synthesis.", J. Am. Chem. Soc., 86, 3068 (1964).

*Primary Examiner*—Paul J. Killos
*Attorney, Agent, or Firm*—J. Frederick Thomsen; William P. Heath, Jr.

[57] ABSTRACT

Disclosed is a process for the preparation of α-acyloxycarbonyl compounds by contacting the corresponding α-dicarbonyl compound with an acyl iodide, which can be employed in an essentially pure form or generated in solution from hydrogen iodide and a carboxylic acid anhydride.

6 Claims, No Drawings

PREPARATION OF α-ACYLOXYCARBONYL COMPOUNDS

This invention concerns a novel process for the preparation of α-acyloxycarbonyl compounds by the chemical reduction of the corresponding α-dicarbonyl compound with an acyl iodide.

Acyloxycarbonyl compounds such as α-acetoxy ketone and α-acetoxy carboxylic acid esters, especially aliphatic α-acetoxy ketones and ester, are useful as flavor and fragrance ingredients in a number of foods and beverages. These compounds have been synthesized by a variety of methods wherein the precursor hydroxy compound is prepared and then acylated.

The reduction of benzils in the presence of aqueous hydrogen iodide and acetic acid to obtain the corresponding benzoin compound is described in J. Am. Chem. Soc., 71, 1585 (1949); 85, 1669 (1963); and 86, 3068 (1964) and in references cited therein. However, when an aliphatic α-diketone was used in this published procedure, the major product was a monoketone which was the result of deoxygenation of one keto group, i.e., one of the carbonyl groups was reduced to a methylene group.

I have discovered a process for preparing α-acyloxycarbonyl compounds from the corresponding α-dicarbonyl compound and avoiding the deoxygenation of the reactant as disclosed in the cited references. The process comprises contacting an α-dicarbonyl compound with a carboxylic acyl iodide.

The α-dicarbonyl compounds which may be used as the reactant in my novel process have the formula

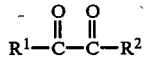  (I)

wherein $R^1$ and $R^2$ each represents an alkyl radical, an aryl radical, an alkoxy radical or an aryloxy radical or $R^1$ and $R^2$ in combination represent an alkylene radical, an oxyalkylene radical or an oxyalkyleneoxy radical. The alkyl and alkoxy radicals represented by $R^1$ and $R^2$ can be the same or different radicals and can be straight- or branched-chain, unsubstituted or substituted alkyl and alkoxy of up to about 14 carbon atoms. The substituents which can be present on the substituted alkyl and alkoxy radicals include alkoxy, aryl, aryloxy, halogen and other groups which are inert to the materials used in the process. Examples of the aryl and aryloxy groups include phenyl, phenyl substituted with alkyl, halogen or alkoxy, naphthyl, naphthyl substituted with alkyl, alkoxy or halogen, phenoxy, phenoxy substituted with alkyl, alkoxy or halogen, naphthyloxy, naphthyloxy substituted with alkyl, alkoxy or halogen. The divalent groups which $R^1$ and $R^2$ collectively may represent may contain from 2 to about 14 carbon atoms such as 1,3-propanediyl, 1,4-butanediyl, 3-oxypropyl (—CH$_2$CH$_2$CH$_2$O—), 2-oxy-1,1-dimethylethyl, 1,3-dioxypropane (—OCH$_2$CH$_2$CH$_2$O—) and the like. The reactants which are most preferred are those in which $R^1$ is alkyl of up to about 4 carbon atoms and $R^2$ is alkyl of up to about 4 carbon atoms, phenyl or tolyl.

The α-acyloxycarbonyl compounds obtained in accordance with the process of my invention have the formula

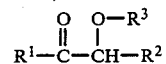  (II)

wherein $R^1$ and $R^2$ are defined above and $R^3$ is a carboxylic acyl group, e.g., containing up to about 12 carbon atoms such as acetyl, propionyl, butanoyl, etc. When the α-dicarbonyl reactant is an unsymmetrical α-diketone, i.e., when $R^1$ and $R^2$ are different alkyl or aryl radicals, the product obtained is a mixture of α-acyloxycarbonyl compounds.

The process requires that the α-dicarbonyl reactant be contacted with at least 2 moles of carboxylic acyl iodide per mole of reactant. The process typically is performed using an excess of acyl iodide of as much as 5 moles of acyl iodide per mole of reactant. The process preferably is performed using about 2 to 3 moles of acyl iodide per mole of reactant. The acyl iodide preferably is acetyl iodide although carboxylic acyl iodides of up to about 12 carbon atoms, e.g., propionyl iodide and butanoyl iodide, may be used.

The acyl iodide employed may be essentially pure or it may be prepared and used as a solution in its corresponding carboxylic acid, for example by mixing hydrogen iodide gas or aqueous hydrogen iodide with a carboxylic acid anhydride. To maximize conversions to and yield of the desired α-acyloxycarbonyl product, the process should be carried out under essentially anhydrous conditions and thus when aqueous hydrogen iodide is used sufficient anhydride normally is used to consume the water of the hydrogen iodide solution. The process normally is conducted in the presence of a carboxylic acid, e.g., an aliphatic carboxylic acid containing up to about 12 carbon atoms, such as is produced when the acyl iodide is obtained from anhydrous or aqueous hydrogen iodide as described above.

Temperature is not critical to the successful operation of the process provided by this invention. For example, temperatures as low as slightly above the freezing point of the acyl iodide or anhydride used and as high as 200° C. may be used. However, the process normally will be conducted at a temperature in the range of about 0° to 125° C. A temperature of about 15° to 25° C. is particularly preferred when the α-dicarbonyl reactant is an α-diketone and about 70° to 80° C. is particularly preferred when the reactant is an α-carbonyl ester, i.e., an α-oxo carboxylic acid, or an α-dicarboxylic acid diester, e.g., diethyl oxalate. Pressures moderately above or below ambient pressure can be used although there normally is no advantage in doing so.

My novel process is further illustrated by the following examples.

PROCEDURE

In each example 8.2 g of 47% aqueous hydrogen iodide (30 mmol hydrogen iodide) was added to 30 mL of ice-chilled acetic anhydride with stirring except in Example 10 an equimolar quantity of propionic anhydride was substituted for the acetic anhydride. The addition should be made with extreme caution since the reaction of aqueous hydrogen iodide is very exothermic and can be deceptive since there is a variable induction period of several seconds to a couple of minutes. After the addition is complete, the reaction mixture is allowed to stir an additional 5 to 10 minutes. During the course of the reaction, hypophosphorous acid, an oxidation inhibitor commonly used in hydrogen iodide solutions, precipitates and is removed from the reaction mixture by filtration through a fine fritted glass filter.

The resulting solution contains acetyl iodide as the predominant iodine species and varies in color from grey to orange-red depending on the source of the aqueous hydrogen iodide. The solution was transferred to a 100 mL, round-bottom flask to which 10 mmol of α-dicarbonyl reactant was added. The reduction of the α-diketones (Examples 1, 2, 3, 4 and 10) was performed with stirring at room temperature for 15 to 20 minutes. The α-ketoesters were reduced by stirring for 15 to 20 minutes at 50° to 55° C. (Examples 8 and 9) or at 70° to 75° C. (Examples 5, 6 and 7).

Each product was isolated by adding, with caution, 10% aqueous sodium bisulfite to the reaction mixture until the orange color of iodine is completely dissipated. The resulting mixture was transferred to a 250 mL separatory funnel and 100 mL water were added. The aqueous layer was extracted three times with 50 mL portions of diethyl ether. The ether layers were combined and back-extracted twice with 50 mL portions of water, 50 mL of 10% aqueous sodium hydroxide and finally with 50 mL of water. The ether phase was dried over potassium carbonate (except in Example 9 in which sodium sulfate was used) and then filtered. The ether then was removed under reduced pressure.

The products were identified based upon their spectroscopic properties and the yields reported are for isolated products except in Example 1 in which yields were determined by gas chromatography analysis and in Examples 4 and 7 in which the yields of the components of the product mixture were determined by integration of the $^1$H NMR spectrum of the crude reaction product mixture after treatment with sodium bisulfite as described above.

The reactants reduced and the products and yields (percent of theory) thereof obtained in Examples 1–10 are shown in the Table. The reactants conform to formula (I) and the products conform to formula (II) in which $R^3$ is acetyl except in Example 10 in which $R^3$ is propionyl. The yields reported for Example 1 are a range of yields achieved in a plurality of biacetyl reductions.

TABLE

| Example | Reactant $R^1$ | Reactant $R^2$ | Products $R^1$ | Products $R^2$ | Yield |
|---|---|---|---|---|---|
| 1 | —CH$_3$ | —CH$^3$ | —CH$_3$ | —CH$_3$ | 93–100 |
| 2 | —C$_6$H$_5$ | —C$_6$H$_5$ | —C$_6$H$_5$ | —C$_6$H$_5$ | 99 |
| 3 | —C$_2$H$_5$ | —C$_2$H$_5$ | —C$_2$H$_5$ | —C$_2$H$_5$ | 88 |
| 4 | —C$_6$H$_5$ | —CH$_3$ | —C$_6$H$_5$ | —CH$_3$ | 55 |
|   |   |   | —CH$_3$ | —C$_6$H$_5$ | 37 |
| 5 | —C$_6$H$_5$ | —OCH$_3$ | —C$_6$H$_5$ | —OCH$_3$ | 95 |
| 6 | —CH$_3$ | —OC$_2$H$_5$ | —CH$_3$ | —OC$_2$H$_5$ | 78 |
| 7 | —CH(CH$_3$)$_2$ | —OC$_2$H$_5$ | —CH(CH$_3$)$_2$ | —OC$_2$H$_5$ | 77 |
| 8 | —C(CH$_3$)$_2$CH$_2$O— | | —C(CH$_3$)$_2$CH$_2$O— | | 50 |
| 9 | —COOC$_2$H$_5$ | —COOC$_2$H$_5$ | —COOC$_2$H$_5$ | —COOC$_2$H$_5$ | 88 |
| 10 | —C$_2$H$_5$ | —C$_2$H$_5$ | —C$_2$H$_5$ | —C$_2$H$_5$ | 98 |

The invention has been described in detail with particular reference to preferred embodiments thereof, but it will be understood that variations and modifications will be effected within the spirit and scope of the invention.

I claim:

1. Process for the preparation of an α-acyloxycarbonyl compound which comprises contacting an α-dicarbonyl compound with at least 2 moles of an acyl iodide per mol of α-dicarbonyl compound, wherein acyl is carboxylic acid acyl.

2. Process according to claim 1 wherein the acyl iodide is formed from hydrogen iodide and a carboxylic acid anhydride and the process is carried out in the presence of a carboxylic acid.

3. Process for the preparation of an α-acyloxycarbonyl compound having the formula

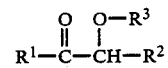

which comprises contacting an α-dicarbonyl compound having the formula

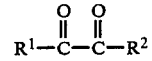

with at least 2 moles of an acyl iodide per mole of α-dicarbonyl compound in the presence of a carboxylic acid, wherein acyl is carboxylic acid acyl and wherein $R^1$ and $R^2$ each represents an alkyl radical, an aryl radical, an alkoxy radical or an aryloxy radical or $R^1$ and $R^2$ in combination represent an alkylene radical, an oxyalkylene radical or an oxyalkyleneoxy radical and $R^3$ represents carboxylic acid acyl of up to about 4 carbon atoms.

4. Process according to claim 3 wherein $R^1$ and $R^2$ each represents alkyl of up to about 14 carbon atoms, alkoxy of up to about 14 carbon atoms or phenyl.

5. Process for the preparation of an α-acetoxycarbonyl compound having the formula

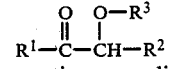

which comprises contacting an α-dicarbonyl compound having the formula

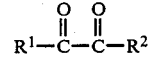

with at least 2 moles of an acetyl iodide per mole of α-dicarbonyl compound in the presence of acetic acid wherein $R^1$ and $R^2$ each represents an alkyl radical, an aryl radical, an alkoxy radical or an aryloxy radical or $R^1$ and $R^2$ in combination represent an alkylene radical, an oxyalkylene radical or an oxyalkyleneoxy radical.

6. Process according to claim 5 wherein $R^1$ and $R^2$ each represents alkyl of up to about 14 carbon atoms, alkoxy of up to about 14 carbon atoms or phenyl.

* * * * *